United States Patent
Wu et al.

(10) Patent No.: US 12,020,815 B2
(45) Date of Patent: Jun. 25, 2024

(54) TRAINING METHOD FOR GIVING TREATMENT RECOMMENDATIONS TO A PHYSICIAN BASED ON A PROPENSITY SCORE AND AN OUTCOME SCORE

(71) Applicant: Siemens Aktiengesellschaft, Munich (DE)

(72) Inventors: Zhiliang Wu, Bayern (DE); Volker Tresp, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 488 days.

(21) Appl. No.: 16/925,671

(22) Filed: Jul. 10, 2020

(65) Prior Publication Data

US 2022/0013230 A1    Jan. 13, 2022

(51) Int. Cl.
*G16H 50/20*     (2018.01)
*G06N 20/00*    (2019.01)
(Continued)

(52) U.S. Cl.
CPC ............ *G16H 50/20* (2018.01); *G06N 20/00* (2019.01); *G16H 10/60* (2018.01); *G16H 50/30* (2018.01); *G16H 50/50* (2018.01); *G16H 50/70* (2018.01)

(58) Field of Classification Search
CPC ........ G16H 50/20; G16H 10/60; G16H 50/30; G16H 50/50; G16H 50/70; G06N 20/00; G06N 3/08; G06N 3/0445
See application file for complete search history.

(56) References Cited

U.S. PATENT DOCUMENTS

2010/0004947 A1 *   1/2010   Nadeau .................. G16H 50/30
                                                                      705/3
2016/0063212 A1 *   3/2016   Monier .................. G16H 10/60
                                                                      705/3
(Continued)

OTHER PUBLICATIONS

Qian et al., "Performance guarantees for individualized treatment rules", Annals of statistics, vol. 39, No. 2, p. 1180, 2011; 2011.
(Continued)

*Primary Examiner* — Michael Tomaszewski
*Assistant Examiner* — Shyam M Goswami
(74) *Attorney, Agent, or Firm* — Schmeiser, Olsen & Watts LLP (57) ABSTRACT

The invention relates to a computer-implemented method for providing a trained function (36) to determine a treatment. To allow a provision of improved treatment recommendations the method comprises the following steps: receiving (S11) a plurality of training data sets (30) each relating to a former patient and each comprising treatment data (31), which represents a former treatment chosen by a physician for the respective former patient, and patient data (32), which relates to a respective health condition of the respective former patient; determining (S12) a propensity score (33), which represents a relative frequency for a former treatment of the plurality to be chosen for each health conditions; determining (S13) an outcome score (34), which is a measure of how the health data (32) and/or the health condition of the respective patient changed; and determining (S14) a treatment recommendation score (35) based on the propensity score (33) and the outcome score (34); and providing (S15) the trained function (36).

10 Claims, 4 Drawing Sheets

(51) Int. Cl.
   *G16H 10/60* (2018.01)
   *G16H 50/30* (2018.01)
   *G16H 50/50* (2018.01)
   *G16H 50/70* (2018.01)

(56) References Cited

U.S. PATENT DOCUMENTS

| | | | | |
|---|---|---|---|---|
| 2019/0325386 | A1* | 10/2019 | Laster | G16H 40/20 |
| 2020/0334566 | A1* | 10/2020 | Vianu | G06N 3/0454 |
| 2023/0170065 | A1* | 6/2023 | De Vries | G16H 50/20 |
| | | | | 705/2 |

OTHER PUBLICATIONS

Choi et al., "Doctor. AI: Predicting clinical events via recurrent neural networks", machine learning for health care conference, 2016, pp. 301-3018; 2016.

Zhao et al., Estimating individualized treatment rules using outcome weighted learning, Journal of the American statistical Association, vol. 107, No. 499, pp. 1106 1118, 2012—Abstract—; 2012.

Bushaev, Vitaly. "How do we train neural networks?", Published in Towards Data Science, 21 pages, Nov. 27, 2017. Retrieved on Jun. 26, 2023 from the Internet: <URL: https://towardsdatascience.com/how-do-we-train-neural-networks-edd985562b73>.

"Neural networks tutorial: Training strategy", 2022, Artificial Intelligence Techniques, Ltd. 14 pages, retrieved on Jun. 26, 2023 from the Internet: <URL: https://www.neuraldesigner.com/learning/tutorials/training-strategy>.

\* cited by examiner

TRAINING METHOD FOR GIVING TREATMENT RECOMMENDATIONS TO A PHYSICIAN BASED ON A PROPENSITY SCORE AND AN OUTCOME SCORE

FIELD OF TECHNOLOGY

The invention relates to a computer-implemented method for providing a trained function to determine a candidate for a treatment. A second aspect of the invention relates to a computer-implemented method for providing treatment recommendation data by applying a trained function. Further aspects of the invention relate to a providing system for providing treatment recommendation data, a training system for providing a trained function and a respective computer program and a respective computer-readable medium relating to the above mentioned methods.

BACKGROUND

The usage of machine learning in the health care sector is known in a different context. For example the prediction of kidney failure from electronic health records of a patient can lead to promising results. A simultaneous prediction of diagnosis and medication prescriptions based on machine learning algorithm, in particular a recurrent neural network (RNN), is known from Choi et al., "Doctor. AI: Predicting clinical events via recurrent neural networks", machine learning for health care conference, 2016, pp 301-3018. Later the recurrent neural network was augmented with attention mechanisms to improve both accuracy and interpretability of the model.

Learning of individualised treatment rules (ITRs) has attracted much attention in the medical research. Learning a better policy from observational data is the basis for building a clinical decision support system. More specifically, the learning of individualised treatment rules (ITRs) is to find a new policy to treat patients for better outcomes. The outcome represents the success of a treatment of a patient. Many recent works focus on such learning tasks with linear models in randomizes clinical trials. However, much more data is recorded in observational studies with more than two treatment options.

To get the highest average outcome, a two-step-method is proposed by Qian et al., "Performance guarantees for individualized treatment rules", Annals of statistics, vol. 39, No. 2, page 1180, 2011. First, an outcome prediction model is fitted with the information of patients and treatments. Then, the individualized treatment rules are derived by selecting the treatment that maximizes the estimation of the outcome model. Such model relies heavily on the correctness of the outcome prediction model.

In comparison, a framework of outcome weighted learning (OWL) to construct a model that directly optimizes the outcome is proposed by Zhao et al., "Estimating individualized treatment rules using outcome weighted learning", Journal of the American statistical Association, vol. 107, No. 499, pp. 1106-1118, 2012. In outcome weighted learning, the learning of individualized treatment rules is formulated as a weighted classification problem and is solved by support vector machines. A separate regression model can be fitted to estimate a baseline so as to compute the residual from the outcome. However, all proposed frameworks above are mainly focused on linear model classes

SUMMARY

It is an object of the present invention to allow a provision of improved treatment recommendations by means of machine learning.

The solution for this object is given by the subject matter of the independent claims. The dependent claims provide advantageous embodiments and improvements.

In the following the same solution according to the invention is described with respect to the claimed providing system and the training system as well as with respect to the claimed methods. Features, advantages or alternative embodiments herein can be assigned to the other claimed objects and vice versa. In other words, claims for the providing system or the training system can be improved with features described or claimed in the context of the methods. In this case, the functional features of the method are embodied by objective units of the providing system or the training system.

Furthermore, in the following the solution according to the invention is described with respect to methods and systems for providing treatment recommendation data as well as with respect to methods and systems for providing a trained function. Features, advantages or alternative embodiments herein can be assigned to the other claimed objects and vice versa. In other words, claims for methods and systems for providing a trained function can be improved with features described or claimed in context of the methods and systems for providing treatment recommendation data, and vice versa.

In particular, the trained function of the methods and the providing system for can be adapted by the methods and systems for training, and vice versa. Furthermore, the input data, in particular the actual health data, can comprise advantageous features and embodiments of the training input data, and vice versa. Furthermore, the output data, in particular the treatment recommendation data, can comprise advantageous features and embodiments of the output training data, and vice versa.

In general, a trained function mimics cognitive functions that humans associate with other human minds. In particular, by training based on training data the trained function is able to adapt to new circumstances and to detect and extrapolate patterns.

In general, parameters of a trained function, for example the propensity score, the outcome score and/or the treatment recommendation score, can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained functions can be adapted iteratively by several steps of training.

In particular, a trained function can comprise a neural network, a support vector machine, a decision tree and/or a Bayesian network, and/or the trained function can be based on k-means clustering, Q-learning, genetic algorithms and/or association rules. In the present case a recurrent neural network proved to be very advantageous for the present tasks. In particular, a neural network can be a deep neural network, a convolutional neural network or a convolutional deep neural network. Furthermore, a neural network can be an adversarial network, a deep adversarial network and/or a generative adversarial network.

A first aspect of the invention relates to a computer-implemented method for providing a trained function to determine a candidate for a treatment, the method comprising the following steps:

receiving a plurality of training data sets each relating to a former patient with each training data set comprising treatment data, which represents a former treatment chosen by a physician for the respective former patient, and patient data, which relates to a respective health condition of the respective former patient at different points in time;

based on the training data sets determining a propensity score for a plurality of former treatments, wherein the propensity score represents a relative frequency for a respective former treatment of the plurality to be chosen for each of the health conditions;

based on the training data sets determining an outcome score for each of the plurality of former treatments, wherein the outcome score is a measure of how the health data and/or the health condition of the respective patient changed between the different points in time, and determining a treatment recommendation score based on the propensity score and the outcome score; and providing the trained function.

Each of the plurality of training data sets may be provided in form of a tuple. Each training data set or each tuple comprises the treatment data and the patient data. Each of the training data sets relates to a respective former patient. The treatment data describes the former treatment which was chosen by the physician or the doctor for the respective former patient. The patient data relates to the respective health condition of the respective former patient, the training data set relates to. The patient data describes the respective health condition of the former patient at different points in time. The different points in time are preferably different points in time in relation to the former treatment. For example the patient data describes the health condition of the former patient at different points in time during, before and/or after the respective former treatment chosen for the patient. the patient data may therefore include one or more measures describing the health condition of the respective former patient at the different points in time. Examples for the health measure are gender, age, static or previous illnesses, body temperature, blood pressure or any other measures suitable for describing the health condition. Especially any measure provided by a sequential electronic health care record (EHR) can be used as health measure and/or be used as part of the patient data.

The treatment data may comprise data relating to the former treatment chosen by the physician or the doctor. For example the treatment data can include parameters describing the former treatment. Generally the treatment data describes the former treatment chosen for the respective patient by the physician or doctor.

Based on the training data sets the propensity score is determined for a plurality of former treatments. The plurality of former treatments may include all former treatments represented in the training data or more specifically in the treatment data. Former treatments which are similar to a predetermined extend may be merged into one former treatment of the plurality. In doing so, former treatments with little or neglectable difference or mismatch can be treated as one common former treatment of a plurality. This can be carried out on the basis of the parameters describing the respective former treatment.

For each of the former treatments of the plurality a relative frequency can be determined as the propensity score. In other words the propensity score is a probability value for a former treatment of the plurality of former treatments to be chosen by a physician. This is carried out with respects to the health conditions in the training data sets. In doing so the propensity score represents the relative frequency for the respective former treatment of the plurality to be chosen depending on the health conditions. Therefore the propensity score can be referred to as a probability distribution or a distribution of the relative frequency for a respective former treatment of the plurality to be chosen for the health conditions. This can be referred to as former policy for treating patients with different former treatments dependent on their health conditions.

Also based on the training data sets the outcome score is determined for each of the plurality of former treatments. The outcome score is a measure of how the health data and/or the health condition of a respective patient changed between the different points in time. The different points in time refer to the different points in time at which the patient data describes the health condition of the respective former patient. In other words it is determined based on the training data sets how the health data or the health condition of the former patient respectively changed during the former treatment. In doing so it can be determined which of the former treatments proofed to be more appropriate for treating the former patient depending on the patient data or the health condition of the former patient respectively. This is carried out for each of the plurality of former treatments. This step can be referred to as learning the outcome of the different former treatments depending on the respective health conditions of the former patients.

Based on the propensity score and the outcome score the treatment recommendation score is determined. Based on the treatment recommendation data recommendations for treating an actual patient can be made in due consideration of a health condition of the actual patient. As the treatment recommendation score is based on the former policy in treating the former patient as well as the outcome of the former treatments the treatment recommendations made on the basis of the treatment recommendation score can be more appropriate in comparison to treatment recommendations in the state of the art. Treatment recommendations based on the treatment recommendation scores are less subject to evaluation errors as they rely on both the former policy of the physicians as well as the observed outcome of the former treatments. One main advantage is, that treatment recommendations based on the treatment recommendation score are less dependent on an outcome model for predicting the outcome of possible treatments for treating the actual patient. On the other hand negative side effects of the former treatments wrong decisions of physicians choosing one of the former treatments for a former patient can be taken into account. Giving an example by the treatment recommendation score it can be taken into consideration that a treatment which is frequently chosen for an illness from which the actual patient is suffering, is inappropriate for the actual patient because of a pre-existing illness of the actual patient.

The trained function obtained by the described steps can be provided for given treatment recommendations for actual patients based on the treatment recommendation score.

The step of receiving the plurality of training data sets can be carried out by a first training interface of the training system. The step of providing the trained function can be carried out by a second training interface of the training system. The steps of determining the propensity score and/or the step of determining the outcome score and/or the determining of the treatment recommendation score can be carried out by a training computation unit of the training system.

In an advantageous embodiment the propensity score and the outcome score are weighted with a weighting score within the step of determining the treatment recommendation score. In other words the treatment recommendation score is determined based on the propensity score and the outcome score wherein the relative influence of the propensity score and the outcome score is determined by the weighting score. The weighting score can determine how much the propensity score contributes to the treatment recommendation score relative to the outcome score. The term "weighting" is to be interpreted widely. The weighting can for example be carried out by calculating fractions, by multiplying, by subtraction or by any arithmetical operation which seems to be appropriate in an individual case. In the latter the weighting by means of subtraction is specified in more detail. In the latter described example the weighting is carried out by reducing the contribution or the influence of the propensity score to the treatment recommendation score by means of subtraction.

Advantageously the weighting is carried out with several different weighting scores, wherein the final weighting score is chosen from the several different weighting scores by a predetermined criterion. In other words several treatment recommendation scores are determined with the different weighting scores. The treatment recommendation score can be determined afterwards by the predetermined criterion. The final weighting score can therefore be determined on the basis of the several treatment recommendation scores. By the predetermined criterion it can be determined which of the several different weighting scores and/or the several treatment recommendation scores is the final weighting score or the treatment recommendation score respectively. In other words the final weighting score can be determined by applying the predetermined criterion on the several different weighting scores and/or the several treatment recommendation scores. In doing so the best relative weight of the propensity score and the outcome score can be learned during the training process.

In an example the weighting is carried out as following: the higher the outcome score for a former treatment of the plurality is, the higher the propensity score is weighted relative to the outcome score. In other words a higher contribution of the propensity score to the treatment recommendation score in comparison to the outcome score is provided with increasing outcome score for a former treatment. Again in other words an increasing weight of the propensity score relative to the outcome score is determined with increasing outcome score. In doing so it can be achieved that the treatment recommendation score is increasingly dependent on the propensity score with increasing outcome of the treatment. This leads to treatment recommendations based on the treatment recommendation score which relies more on former treatment choices of the physicians if the outcome was good and/or rely less on the former treatment choices made by the physicians if the outcome was less good. In doing so the treatment recommendations allow physicians to learn from former bad choices.

According to a further development it is envisaged that the health data, which is received, includes static and sequential health data. This regards especially the health data which is part of the plurality of training data sets. It can be envisaged that only the sequential health data relates to the respective health condition of a respective former patient at the different points in time (especially during the former treatment). In contrary, the static health data describes additional static measures of the health state. The static measures can be regarded as invariant and therefore be valid for all of the different points in time. The static health data can add background information to the sequential health data. Examples for static health data are gender, age, nationality, pre-existing illnesses and so on. By separation in static and sequential health data the complexity of the health data and the complexity of determining the outcome score can be reduced.

According to a further development it is envisages that a treatment matching factor, which is a measure for a discrepancy between the treatment recommendation score and the propensity score is determined. In other words the treatment matching factor is calculated as a measure for how much the treatment recommendation score and the propensity score differ. Again in other words a deviation between the treatment recommendation score and the propensity score is determined or calculated. A measure for the deviation can be provided by the treatment matching factor. The treatment matching factor may indicate how much a new policy to treat an actual patient differs from the former policy for treating the former patients. Therein the new policy can be defined by the treatment recommendation score. The advantage of determining the measure for the discrepancy is that huge differences in the new and old policy can be recognized.

According to a further development it is envisaged that an error message is output when the discrepancy represented by the treatment matching factor exceeds a predetermined limit. The error message can indicate that the difference between the former policy and the new policy of treating a patient is bigger than a certain extend. In other words the error message is output when the difference between the treatment recommendation score and the propensity score exceeds the predetermined limit. Due to the error message it is possible to warn a user that treatment recommendations made on the basis of the treatment recommendation score do not comply with the former policy of treating the patient.

A second aspect of the present invention relates to a computer-implemented method for providing treatment recommendation data, comprising:
 receiving actual patient data, which relates to a health condition of an actual patient;
 applying a trained function by a machine learning algorithm to the actual patient data, wherein the treatment suggestion data is generated by use of a treatment recommendation score,
 wherein at least one parameter of the trained function is based on a propensity score, which represents a relative frequency for a specific treatment to be chosen by a physician for specific health conditions of a former patient, and/or at least one parameter of the trained function is based on an outcome score, which is a measure of how health data and/or a health condition of the former patient changed while applying the specific treatment,
 providing the treatment recommendation data.

The receiving of the actual patient data can be carried out by a first interface of a providing system for providing the treatment recommendation data. The providing of the treatment recommendation data can be carried out by a second interface of the providing system. The applying of the trained function can be carried out by a computation unit of the providing system.

The treatment recommendation data which is provided can be determined based on the treatment recommendation score. The treatment recommendation data can include a treatment recommendation. The treatment recommendation can be a recommendation of how to treat the actual patient based on the actual patient data.

At least one parameter of the trained function, in particular the treatment recommendation score, can be based on the propensity score. Additionally or alternatively, at least one parameter of the trained function, in particular the treatment recommendation score, can be based on the outcome score. According to a further development the at least one parameter, in particular the treatment recommendation score, can be based on both, the propensity score and the outcome score. The propensity score represents the relative frequency for a specific treatment to be chosen by a physician for a specific health condition of a former patient. The outcome score is a measure of how health data and/or a health condition of the former patient changed while applying the specific treatment. The propensity score described in the context of the method for providing the treatment recommendation data may be the same propensity score, which is described in the context of the method for providing the trained function. The outcome score described in the context of the method for providing the treatment recommendation data may be the same outcome score, which is described in the context of the method for providing the trained function. The treatment recommendation score described in the context of the method for providing the treatment recommendation data may be the same treatment recommendation score, which is described in the context of the method for providing the trained function.

The actual patient data can have the same properties as the former patient data. For example the actual patient data can have the same data structure as the former patient data. Alternatively of additionally, the actual training data may include at least one of the health parameters included in the former patient data. Of course the health parameters comprised by the actual patient data relates to the actual patient. In other words the actual patient data may comprise a plurality of health parameters relating to the actual patient.

According to a further development it is envisaged, that the trained function which is applied to the actual patient data by the machine learning algorithm is provided by the method of the first aspect of the invention. In other words the trained function may be provided by the method for providing a trained function which is part of the present invention.

Another aspect of the invention related to a providing system, comprising:
  a first interface, configured for receiving actual patient data which relates to a health condition of an actual patient;
  a second interface, configured for providing the treatment recommendation data,
  a computation unit, configured for applying a trained function to the actual patient data, wherein the treatment recommendation data is generated,
  wherein at least one parameter of the trained function is based on a propensity score, which represents a relative frequency for a specific treatment to be chosen by a physician for specific health conditions of a former patient, and/or at least one parameter of the trained function is based on an outcome score, which is a measure of how health data and/or a health condition of the former patient changed while applying the specific treatment.

The providing system may comprise a computer, a server, a micro controller or an integrated circuit. Alternatively the providing system may comprise a cluster or cloud of computers.

The providing system comprises the first interface, the second interface and the computation unit. The computation unit may comprise hardware-elements or software-elements for performing computation operations, in particular the applying of the trained function. Examples for hardware-elements are a microprocessor, a digital signal processor, a FPGA (field programmable gate array) of the like. Additionally the computation unit can comprise a memory unit. The memory unit can be provided by non-permanent memory, for example random access memory (RAM) or as permanent memory, for example hard disc, USB stick, SC card, solid state disc or the like. The first interface and/or the second interface can be a hardware-interface and/or a software-interface (for example PCI-bus, USB or fire wire).

A further aspect of the invention relates to a computer program comprising instructions which, when the program is executed by a providing system, cause the providing system to carry out the method for providing treatment recommendation data. The computer program can be made for being executed on the above-mentioned providing system. The computer program can for example be loaded into the memory unit of the computation unit and be executed by the computation unit.

A further aspect of the present invention relates to a computer-readable medium comprising instructions which, when executed by a providing system, cause the providing system to carry out the method for providing treatment recommendation data. The computer-readable medium may be a permanent or a non-permanent memory. An example for non-permanent memory is random access memory (RAM). Examples for permanent memory are optical storage mediums, for example Cd or DVD, hard discs, solid state discs, memory cards and the like.

Another aspect of the invention related to a providing system, comprising:
  a first training interface, configured for receiving a plurality of training data sets each relating to a former patient with each training data set comprising treatment data, which represents a former treatment chosen by a physician for the respective former patient, and patient data, which relates to a respective health condition of the respective former patient at different points in time,
  a training computation unit, configured for training a function based on the based on the training data sets,
  wherein the training computation unit is configured for determining a propensity score for each of the former treatments, wherein the propensity score represents a relative frequency for the respective treatment to be chosen for each of the health conditions,
  wherein the training computation unit is also configured for determining an outcome score for each of the former treatments, wherein the outcome score is a measure of how the health data and/or the health condition of the respective patient changed between the different points in time; and
  and wherein the training computation unit is also configured for concatenating the propensity score and the outcome score to a combined score,
  a second training interface, configured for providing the trained function.

The training system may comprise a computer, a server, a micro controller or an integrated circuit. Alternatively the training system may comprise cluster or cloud of computers.

The training system comprises the first interface, the second interface and the computation unit. The computation unit may comprise hardware-elements or software-elements for performing computation operations, in particular the applying of the trained function. Examples for hardware-elements are a microprocessor, a digital signal processor, a FPGA (field programmable gate array) of the like. Additionally the computation unit can comprise a memory unit. The memory unit can be provided by non-permanent memory, for example random access memory (RAM) or as permanent memory, for example hard disc, USB stick, SC card, solid state disc or the like. The first interface and/or the second interface can be a hardware-interface and/or a software-interface (for example PCI-bus, USB or fire wire).

A further aspect of the invention relates to a computer program comprising instructions which, when the program is executed by a training system, cause the training system to carry out the method for providing treatment recommendation data. The computer program can be made for being executed on the above-mentioned training system. The computer program can for example be loaded into the memory unit of the computation unit and be executed by the computation unit.

A further aspect of the present invention relates to a computer-readable medium comprising instructions which, when executed by a training system, cause the training system to carry out the method for providing treatment recommendation data. The computer-readable medium may be a permanent or a non-permanent memory. An example for non-permanent memory is random access memory (RAM). Examples for permanent memory are optical storage mediums, for example Cd or DVD, hard discs, solid state discs, memory cards and the like.

In the following the invention is described further on the basis of the FIG. Features, advantages our alternative embodiments shown in the FIG can be assigned to the claimed objects. In other words the method for providing the function, the method for providing treatment recommendation data, the providing system and the training system can be improved with features described or shown in the FIG.

BRIEF DESCRIPTION

It is shown.

DETAILED DESCRIPTION

Figure 1:
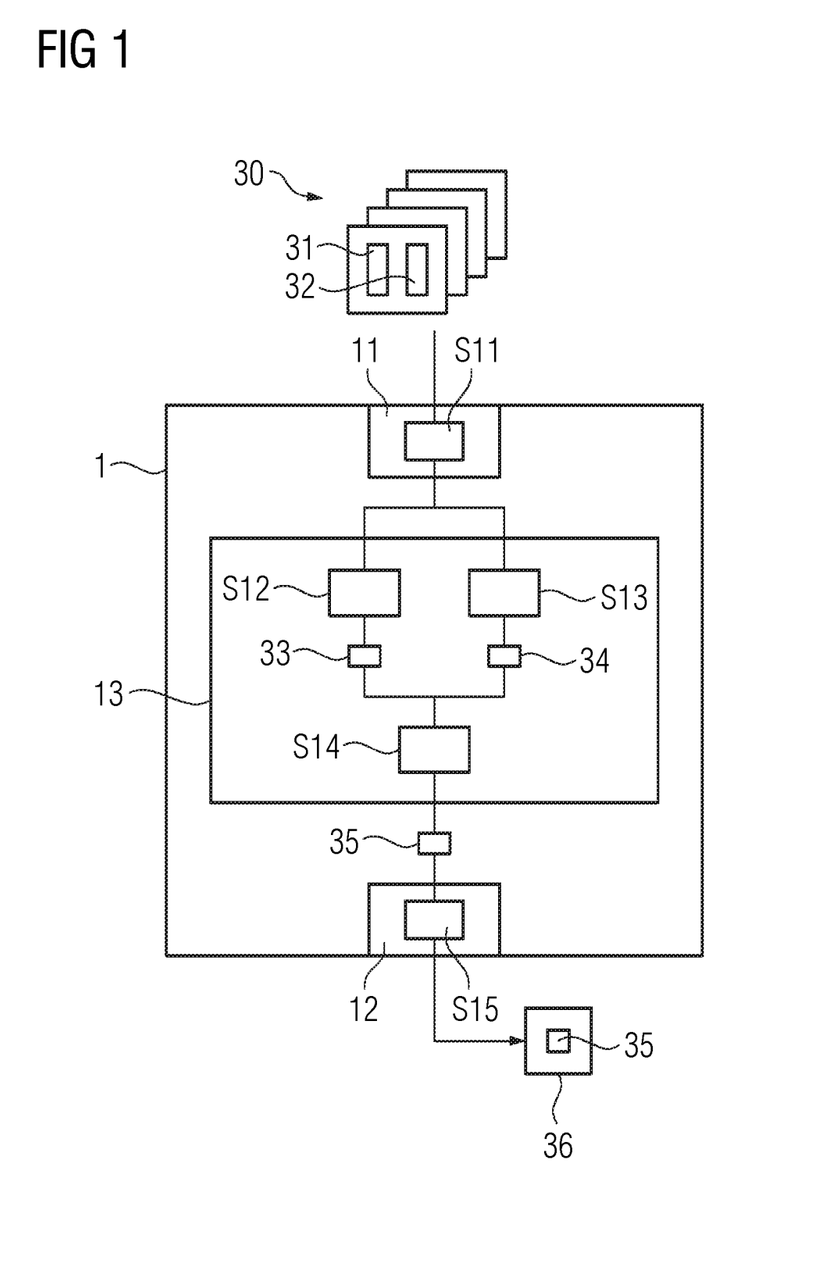
FIG. 1 a block diagram of a training system carrying out the steps of a computer-implemented method for providing a trained function.

FIG. 1 shows a training system 1 comprising a first training interface 11, a second training interface 12 and a training computation unit 13. The first training interface 11 is configured for receiving a plurality of training data sets 30 each relating to a former patient. With each training data set 30 comprising treatment data 31 and patient 32. The treatment data 31 represents a former treatment chosen by a physician for the former patient the respective training data set 30 is relating to. The patient data 32 relates to a health condition of the former patient at different points in time in relation to the chosen treatment. So each of the training data sets contains the treatment data 31 and health data 32 relating to health and treatment of the same former patient. The training data sets 30 of the plurality can relate to different former patients. The treatment data 31 describes the former treatment with that the former patient has been treated. The former treatment can be described by one or more treatment parameters. The description of the health condition of the respective former patient by the health data 32 is described in more detail in the context of FIG. 4.

After the receiving of the training data sets 30 by the first training interface 11 in the step S11 following steps S12 and S13 are carried out. The steps S12 and S13 can be carried out at the same time or one after each other. The steps S12, S13 and a following step S14 are carried out by the training computation unit 13 in the present case. The training computation unit 13 can be provided by a microprocessor, a digital signal processor or a field programmable gate array (FPGA) or the like. In the step S12 a propensity score for a plurality of former treatments is determined based on the training data sets 30. The propensity score 33 represents a relative frequency for a respective former treatment of a plurality to be chosen for each of the health conditions indicated by the health data 32. In other words the propensity score connects the treatment data 31 and the health data 32 to learn which former treatments have been chosen by the independency of the health condition. The propensity score may include a distribution of the relative frequency for the former treatments independency of the health data 32 or the health condition respectively.

In the step S13 an outcome score 34 is determined based on the training data sets 30. The outcome score 34 is a measure of how the health data 32 or the health condition respectively changes between the different points in time while treating the former patient with the respective former treatment chosen by the physician. In other words by determining the outcome score 34 it is learned by the system how the former treatments affected the health data 32 or the health condition of the former patient respectively. In other words the outcome score 34 is a measure of the outcome or the effectiveness of the different former treatments in dependency of the respective health conditions. The outcome score 34 can be based on observations from the former health data 32. The determination can be carried out in a way that the former health data 32 is evaluated to determine the change of the health condition of the former patient during the former treatment. This change can be considered or defined as caused by the former treatment. The outcome score is determined as such that it describes the change of the health condition according to the former health data 32.

Alternatively the outcome score 34 is part of the training data sets 30. In this case the outcome score 34 can for example be received as part of the former health data 32. In this case during the step S13 the outcome score 34 is acquired from the training data sets 3. Optionally it is possible to accumulate the outcome score 34 over the different training data sets 30. For example it is possible to average the preliminary outcome scores acquired from two different training data sets 30 of to the final outcome score 34 if the former patient, to which the two different training data sets 30 relate, have a similar health condition and were treated similarly.

In the following step S14 a treatment recommendation score 35 is determined based on the propensity score 33 and the outcome score 34. This is carried out in a way that both the propensity score 33 and the outcome score 34 contribute to the treatment recommendation score 35. In the present example the propensity score 33 and the outcome score 34 are weighted with a weighting score in the step S14. The weighting score defines how much the outcome score 34 and the propensity score 33 contribute to the treatment recommendation score 35 relative to each other. The weighting is carried out in the latter described example algorithm in line 3 and line 4. The weighting score is the parameter $\lambda_j$ in the example algorithm. The weighting score $\lambda_j$ reduces the impact of the physician policy, which is indicated by the propensity score, by means of subtraction. The bigger the value for $\lambda_j$, the smaller is the impact of the former policy of the physician or the impact of the propensity score 33 on the treatment recommendation score 35.

In step S15 the trained function 36 is provided. The trained function 36 comprises the treatment recommendation score 35 by means of which a treatment recommendation for an actual patient can be given on the basis of actual patient data 37 relating to a health condition of the actual patient. This is described in the following referring to FIG. 2.

Figure 2:
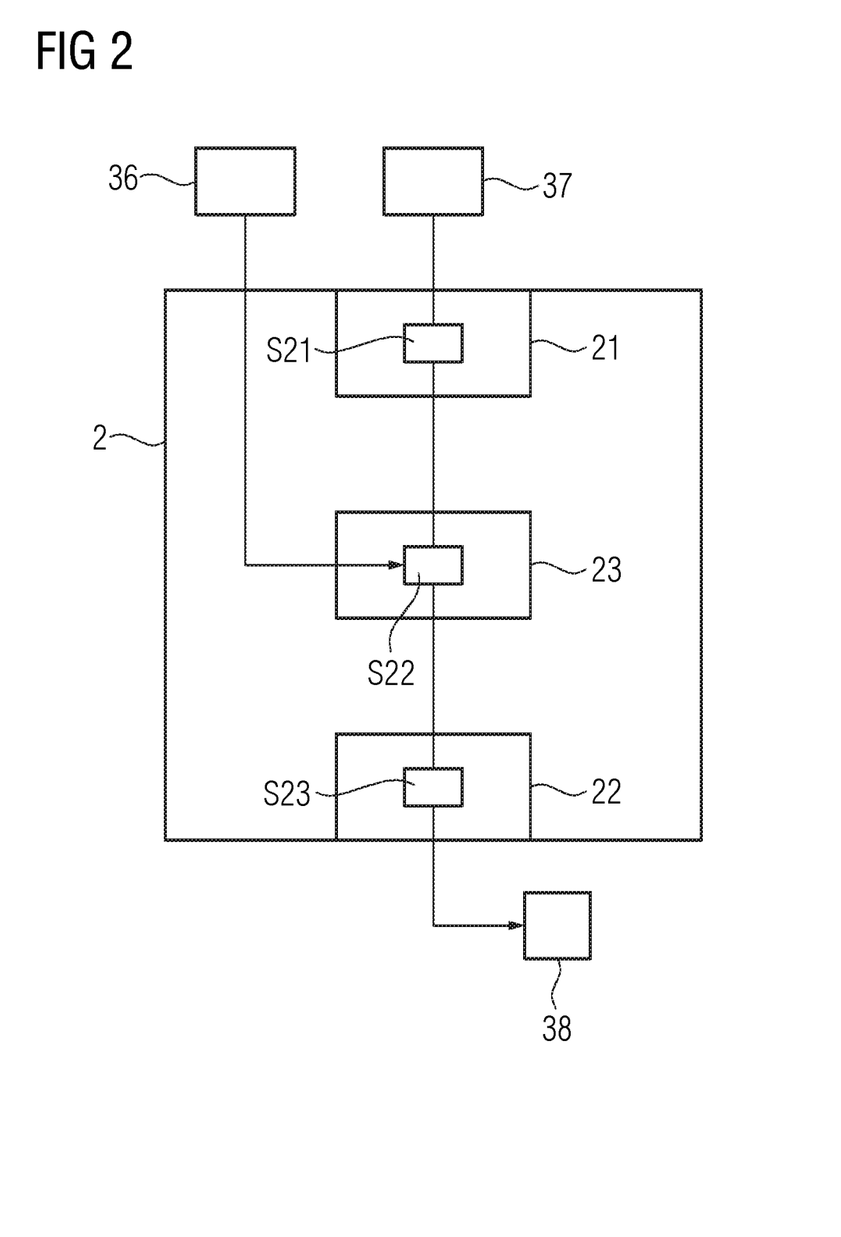
FIG. 2 a block diagram of a providing system carrying out the steps of a computer-implemented method for providing treatment recommendation data.

FIG. 2 shows a providing system 2 comprising a first interface 21, a second interface 22 and a computation unit 23. In a step S21 the actual patient data 37 is received. The actual patient data 37 relates to the health condition of the actual patient. For example the actual patient data 37 can describe the health condition of the actual patient by providing a plurality of health parameters. The actual patient data 37 can be based on the same data structure and/or health parameters as the health data 32. Therefore the actual patient data is also described by FIG. 4 in the latter. In a step S22 the computation unit applies a trained function, in particular the trained function 36 from the method of FIG. 1, to the actual patient data 37. In doing so treatment suggestion data 38 is generated by use of the treatment recommendation score 35 which is part of the trained function 36. One parameter of the trained function, namely the treatment recommendation score 35, is based on the propensity score 33, which represents the relative frequency for a specific treatment to be chosen by a physician for specific health conditions of a former patient. The same parameter is also based on the outcome score 34, which is the measure of how health data and/or health condition of the former patient changed while applying the specific treatment. By applying the trained function 36 which the treatment recommendation score 35 the treatment recommendation score 35 can determine the treatment recommendation data 38.

In a step S23 the treatment recommendation data, which is implying a treatment recommendation for how to treat the actual patient, is provided or output by the second interface 22. The treatment recommendation data 38 or the treatment recommendation therein can be for example provided to a physician to support him in making his treatment decision how to treat the actual patient.

Figure 3:
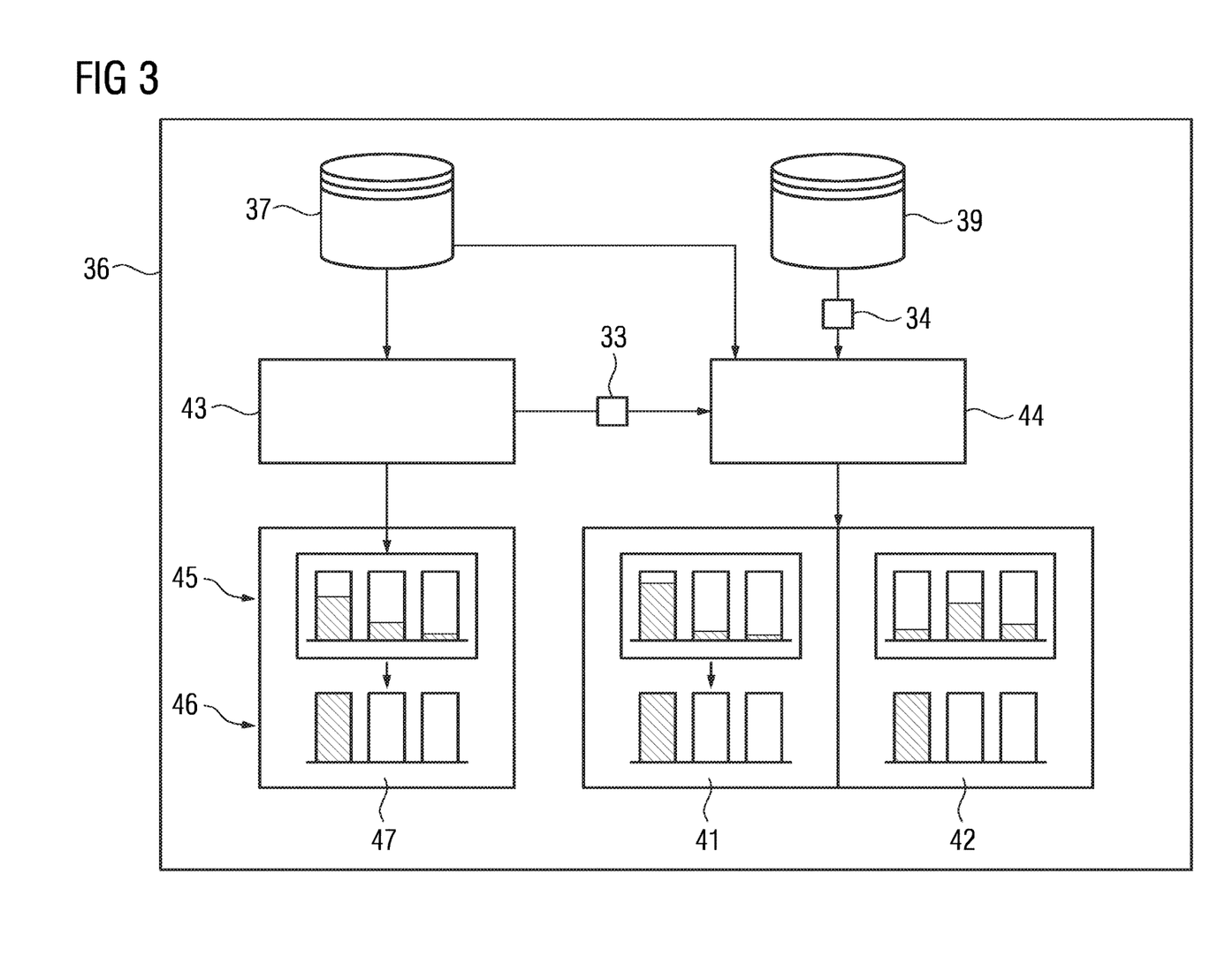
FIG. 3 a block diagram of a proposed frame work for a trained function.

FIG. 3 shows an exemplary frame work for the trained function 36. Based on the actual patient data 37 and outcome data 39 a treatment decision can be made which is output as part of the treatment recommendation data 38. From the patient data 37 a predictive modelling of treatment decisions is carried out in a modelling block 43. This can also be referred to as predicting a respective possibility for different treatments to be chosen. This is mainly bases on the former policy of the physician. Based on that the propensity score 33 can be calculated. The relative frequency for the different treatments to be chosen is provided in column 47. In row 45 the output distribution corresponds to the predictive modelling of the treatment to be chosen. So row 45 in column 47 contains a probability distribution for the plurality of treatments to be chosen. This prediction or the probability distribution is based on the propensity score 33. Row 46 in column 47 contains a true prescription for a treatment which has been made by physicians in a former case according to the patient data 37. So the patient data 37 can additionally include prescriptions which have already been chosen for the actual patient, to whom the patient data 37 relates.

The propensity score 33 can be provided to an individualized treatment rule block 44. In this block 44 the propensity score 33 and an outcome score derived from the outcome 38 are put together to predict a respective outcome of the different treatments. In FIG. 3 there are two different examples included. In the first example visualized in column 41 the predicted outcome for the prescription according to column 47 is good. In the second example visualized in column 42 the predicted outcome for the prescription according to column 47 is bad. Row 45 of column 41 and 42 relates to row 45 of column 47. Row 46 of column 41 and 42 relates to row 46 of column 47. Therefore in columns 41 and 42, row 45 refers to the prediction or the probability distribution is based on the propensity score 33. Row 46 refers to the true prescription of the physicians (observed in the dataset).

So the left side of the diagram models treatment decision is focussing on mimicking the physician's treatments chosen in the past. Without taking outcome information 38 into consideration the performance of the treatment recommendation is limited to the performance of the physicians. On the other hand by considering the outcome information 38 a better performance can be provided. When the outcome for the most probable choice or the prescription of the physician is positive, then the trained function 36 will follow the former policy of the physicians (see example in column 41). When the outcome for the most probable treatment to choose or the prescription of the physician is negative, then the training system 36 will give a different recommendation (see example in column 42). The learned individual treatment rules have a potential to improve the clinical choices in how to treat patients.

In summarization there are two main parts of the proposed framework: a predictive model of the treatment decision and a propensity score-based loss layer. The extracted dataset can be in the form of $\{(X_{seq})_i, (x_{sta})_i, \alpha_i, \delta_i\}_{i=1}^m$, where $X_{seq}$ denotes the (multi-variate) random variable for the sequential information, $x_{sta}$ for the static information, $\alpha$ for the treatment option, and $\delta$ denotes the corresponding loss for the observed treatment. Scalars are denoted by lowercase letters like a; (column) vectors are denoted by bold lowercase letters like $x_{sta}$; matrices are denoted by uppercase letter like $X_{seq}$; sets are denoted by calligraphic letters like $\mathcal{A}$.

Figure 4:
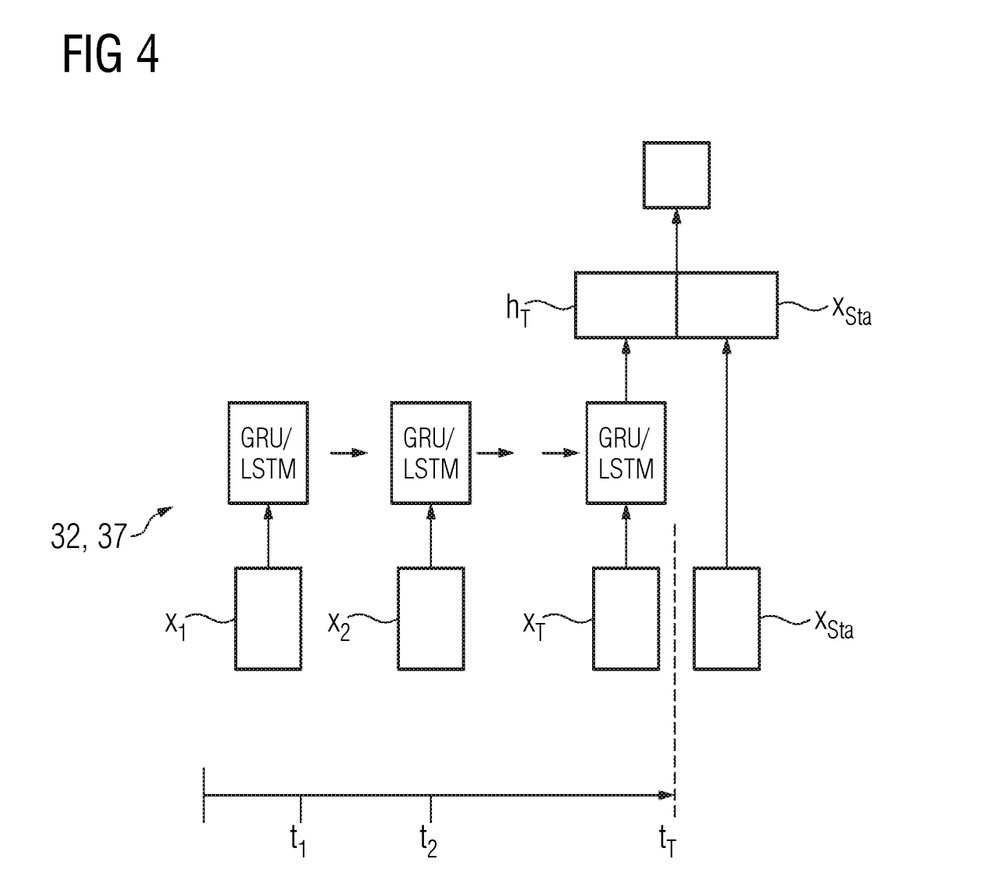
FIG. 4 a block diagram of a patient representation by the patient data.

As a generalization of the feedforward neural networks, recurrent neural networks (RNNs) have a natural property of modeling sequential data. Da data structure of the health data 32 or actual patient data 37 is depicted in FIG. 4. Formally, given an input sequence $(x_1, x_2, \ldots, x_T)$ of health data 32 or actual patient data 37, the RNN updates the hidden states h at time step t (which corresponds to the different points in time mentioned above) iteratively by $$h_t = g(Wx_t + Uh_{t-1}),$$

where $g(\cdot)$ is usually a smooth, bounded function like the logistic sigmoid function. Classification or regression could be realized by adding models on top of the hidden state $h_t$, resulting in various RNN types for different sequential prediction tasks. However, classical RNNs suffer from the vanishing gradient problem and therefore fail to capture long-term dependencies from the past inputs, in particular former health data 32. More advanced variants of RNNs, Gated Recurrent Unit (GRU) and Long Short-Term Memory (LSTM), are proposed to solve the problem with gating mechanisms and have achieved great successes in modeling sequential data with long-term dependencies, such as texts or sensory data.

In the case of predictive modeling of treatment decisions, the extracted multidimensional vector $x_t$ at different time-steps form the sequential input data $X_{seq}$. GRU/LSTM are used to encode such information into the hidden states $h_t$. As we are mainly interested in modeling the treatment decisions, a many-to-one structure is used, i.e., only the representation of the last hidden state $h_T$ is utilized as the input for the treatment prediction, where T is the number of (observed) time-steps before the treatment. Formally, we have GRU/LSTM: $\mathbb{R}^{T \times f_d} \to \mathbb{R}^h$ $X_{seq} \mapsto h_T$, where $f_d$ is the number of dynamic features, h is the dimension of the hidden state and will be tuned as a hyper-parameter in the experiments. The static information is concatenated with the hidden state encoded by GRU/LSTM, so that the static information is included for the modeling of the treatment decisions. Formally, we have $z = (h_T, x_{sta})$.

The resulting vector $z \in \mathbb{R}^{h+f_s}$ represents the patient's complete medical history in a latent vector space and facilitates different tasks on top of it. In the simplest case, a softmax classifier is built on top of it for the treatment prediction as illustrated in the following figure.

The trained function, in particular the(deep) neural network mentioned above, can be viewed as a stochastic policy learned from the physicians, the physicians' policy, like also mentioned. It outputs a conditional probability distribution $\hat{\mathbb{P}}(\alpha | \cdot)$ over treatments $\mathcal{A} = \{1, 2, \ldots, 25\}$. Although the treatments are observed in a deterministic fashion, such probability reflects the recommended score of a certain treatment, given the characteristics of the patients, which is also known as the propensity score in the medical domain. We define the complete medical history including static and sequential information as $X := \{X_{seq}, x_{sta}\}$, and the estimated propensity score $\hat{\mathbb{P}}(\alpha = n | X)$ (reference sign 33 in FIG. 1 and FIG. 2) is also referred to as the output of the physicians' policy. How physicians make a treatment decision with uncertainty (according to the clinical guidelines) can be viewed as sampling a treatment according to the true propensity score $\hat{\mathbb{P}}(\alpha = n | X)$. In most cases, it would be the treatment with the highest true propensity score.

Following the formulation in batch learning bandit feedback (BLBF), the goal of learning the optimal ITRs is to find a new policy $\pi_w$ that minimizes the risk defined as $$r(\pi_w) = \mathbb{E}_{X \sim \mathbb{P}(X)} \mathbb{E}_{a \sim \pi_w(\mathcal{A}|X)} [\delta(X, a)] \qquad (1)$$

$$= \mathbb{E}_{X \sim \mathbb{P}(X)} \mathbb{E}_{a \sim \mathbb{P}(\mathcal{A}|X)} \left[ \delta(X, a) \cdot \frac{\pi_w(a|X)}{\mathbb{P}(a|X)} \right],$$

where w denotes the parameters of the new policy. The second equation involves the importance sampling to remove the distribution mismatch between the physicians' policy and the new policy. Intuitively speaking, the new policy $\pi_w$ will have a lower expected risk $r(\pi_w)$ when it is more certain of the treatment with positive outcome and is less confident of the treatment with negative outcome.

The Inverse Propensity Score (IPS) estimator applies the Monto Carlo Sampling to estimate the expected risk in Eq. 1 as $$\hat{r}_{IPS}(\pi_w) = \frac{1}{m} \sum_{i=1}^{m} \delta_i \frac{\pi_w(a_i | X_i)}{\mathbb{P}(a_i | X_i)}. \qquad (2)$$

The IPS estimator would be unbiased if we have enough understanding of the physicians' policy. Therefore, it is appealing to apply the risk defined by the IPS estimator (IPS risk) in the cost function to learn the optimal ITRs.

However, there are mainly two reasons for not using the IPS risk directly. On one hand, it is well known that the IPS estimator suffers from large variance if there is a large discrepancy between the new policy and the physicians' policy, which would be more serious for high-capacity models like neural networks in our case. On the other hand, with the introduction of the propensity score $\hat{\mathbb{P}}(\alpha_i | X_i)$ into the IPS estimator, directly minimizing it will lead to a severe problem called propensity score overfitting. In short, the new policy tends to minimize the IPS risk through fitting itself by avoiding the treatments from the physicians policy, instead of learning the treatment with low loss. In the present case, the minimal IPS risk in Eq. 2 would be 0. To achieve it, the new policy would simply put zero probability on all the observed treatments from the physicians' policy. In other words, the new policy would achieve the minimal IPS risk by recommending any treatment different from the physicians', which is obviously inappropriate. In the following experiment section, such phenomenon will also be empirically verified. In addition, if we define the loss as −1 for the positive outcome and 0 for the negative outcome, the new policy would minimize the IPS risk by simply putting more probability on the observed treatments, which is also not what we want.

The propensity score overfitting is caused by the lack of equivariance of the IPS estimator, which means the minimizer of IPS risk changes by a translation of the loss. Formally, the minimizer of the expected risk in Eq. 1 would not change with a constant shift c in loss as $$\min_{w} \mathbb{E}_{X \sim \mathbb{P}(X)} \mathbb{E}_{a \sim \mathbb{P}(\mathcal{A}|X)} \left[ [\delta(X, a) + c] \cdot \frac{\pi_w(a|X)}{\mathbb{P}(a|X)} \right] ==$$

$$c + \min_{w} \mathbb{E}_{X \sim \mathbb{P}(X)} \mathbb{E}_{a \sim \mathbb{P}(\mathcal{A}|X)} \left[ \delta(X, a) \cdot \frac{\pi_w(a|X)}{\mathbb{P}(a|X)} \right]$$

where the equation holds because of the linearity of the expectation and $$\mathbb{E}_{X, a} \left[ \frac{\pi_w(a|X)}{\mathbb{P}(a|X)} \right] = 1.$$

However, the IPS estimator doesn't have the following property since $$\min_{w} \frac{1}{m} \sum_{i=1}^{m} (\delta_i + c) \frac{\pi_w(a_i | X_i)}{\mathbb{P}(a_i | X_i)} \neq c + \min_{w} \frac{1}{m} \sum_{i=1}^{m} \delta_i \frac{\pi_w(a_i | X_i)}{\mathbb{P}(a_i | X_i)},$$

due to the unconstraint of the treatment matching factor (TMF) defined as $$s(\pi_w) := \frac{1}{m} \sum_{i=1}^{m} \frac{\pi_w(a_i \mid X_i)}{\mathbb{P}(a_i \mid X_i)},$$

which will be far from 1 if there occurs the propensity score overfitting problem. The self-normalized IPS estimator (SNIPS) is proposed by integrating the treatment matching factor into the estimator as $$\hat{r}_{SNIPS}(\pi_w) = \frac{\frac{1}{m}\sum_{i=1}^{m} \delta_i \frac{\pi_w(a_i \mid X_i)}{\mathbb{P}(a_i \mid X_i)}}{s(\pi_w)} = \frac{\frac{1}{m}\sum_{i=1}^{m} \delta_i \frac{\pi_w(a_i \mid X_i)}{\mathbb{P}(a_i \mid X_i)}}{\frac{1}{m}\sum_{i=1}^{m} \frac{\pi_w(a_i \mid X_i)}{\mathbb{P}(a_i \mid X_i)}}, \quad (3)$$

which enjoys the property of equivariance, i.e., the minimizer will thus keep the same regardless of any translation of the loss, focusing on minimizing the "true" risk.

Meanwhile, the optimization problem including the SNIPS estimator cannot be solved directly by stochastic gradient decent-based method, as all the samples are required to compute the denominator. A batch of samples could be used to estimate it, but the result can be biased. To solve this problem a so called "BanditNet" can be used by reformulating the SNIPS estimator with an additional constraint. We take advantage of the proposed reformulation to learn the optimal ITRs for sequential EHRs.

Finally, in the persent setting, one problem remains to be solved, namely the true propensity score $\hat{\mathbb{P}}(\alpha=\alpha_i|X)$ is not in our dataset, which is necessary in either training or evaluating the ITRs. Therefore, we propose to use the estimated propensity score $\hat{\mathbb{P}}(\alpha=\alpha_i|X)$ from the predictive model trained in the last section to replace it. In the following experiment section, the performance of such estimation will be shown. Besides, some recent works prove that such estimation makes the estimator asymptotically unbiased.

The underlying formulas of the whole framework, which is also depicted in FIG. 3, are summarized as below.

| | Algorithm 1: etIPS |
|---|---|
| | Input: A dataset of the form $\{X_i, a_i, \delta_i\}_{i=1}^{m}$ |
| | Output: The policy of the optimal ITRs, $\pi_{w^*}(a|X)$ |
| 1 | Learn the physicians' policy $\hat{\mathbb{P}}(a|X)$ with $\{X_i, a_i\}_{i=1}^{m}$ with the network structure in Fig. 3. |
| 2 | Compute the estimated propensity score for the observed treatment as $\hat{p}_i := \hat{\mathbb{P}}(a = a_i|X_i)$ |
| 3 | for $\lambda_j \in \{\lambda_i, \ldots, \lambda_k\}$ do |
| 4 | $\quad w_j^* \leftarrow \mathrm{argmin}_{w_j} \left\{ \frac{1}{m}\sum_{i=1}^{m} (\delta_i - \lambda_j) \frac{\pi_{w_j}(a_i \mid X_i)}{\hat{p}_i} \right\}$ |
| 5 | $\quad s_j \leftarrow \frac{1}{m}\sum_{i=1}^{m} \delta_i \frac{\pi_{w_j^*}(a_i \mid X_i)}{\hat{p}_i}$ |
| 6 | end |
| 7 | $s^*, w^* \leftarrow \mathrm{argmin}_{j, w_j^*} \left\{ \frac{1}{s_j} \frac{1}{m}\sum_{i=1}^{m} \delta_i \frac{\pi_{w_j}(a_i \mid X_i)}{\hat{p}_i} \right\}$ |
| 8 | return $\pi_{w^*}(a|X)$ |

In line 1, the propensity score is estimated with the physicians' policy to augment the original dataset. In addition, the cost function defined in line 4 is minimized on top of the neural network for the physicians' policy introduced above. Instead of minimizing the cross-entropy loss as learning the physicians' policy, the estimated propensity score-based risk is applied in the loss layer to learn the new policy for the optimal ITRs. Furthermore, the difference between the minimization goal in line 4 and the IPS risk in Eq. 2 is the translation $\lambda_j$, which is also referred to as weighting score. Therefore, we name the algorithm as estimated translated Inverse Propensity Score (etIPS). As mentioned earlier, a translation of the loss results in a difference between the minimizers of the IPS risk: the new policy tends to avoid the treatments in the physicians' policy for positive losses whereas it prefers to over-present the physicians' policy for negative losses. With tuning the hyper-parameter $\lambda_j$, the method finds the optimal translation to balance such two tendencies, which can also be viewed as a variant of the baseline definition. The final minimization step in line 7 ensures the resulting new policy to have the lowest SNIPS risk in Eq. 3 by putting $s_j$ in the denominator to penalize small treatment matching factors. Intuitively speaking, the found optimal translation $\lambda^*$ enables the new policy to be trained through encouraging the network to learn both from the great moments of the physician (treatments with positive outcome) as well as unsuccessful cases (treatments with negative outcome).

The invention claimed is:

1. A computer-implemented method for providing a trained function to determine a candidate treatment recommendation for treating an actual patient, said method comprising:

training, by a processor, a neural network using a plurality of training data sets respectively corresponding to a plurality of different former patients, each training data set being specific to a respective former patient of the plurality of different former patients, each training data set comprising treatment data pertaining to a former treatment of a plurality of former treatments chosen by a physician for the respective former patient, and each training data set comprising health data pertaining to a respective health condition of the respective former patient at different points in time, said using a plurality of training data sets including using the treatment data and the health data, said trained function comprising the neural network, said neural network determines treatment recommendation data that includes the candidate treatment recommendation for treating the actual patient, said training the neural network comprising determining parameters of the neural network, said parameters comprising: (i) a propensity score for each respective former treatment of the plurality of former treatments, wherein the propensity score represents a relative frequency for each respective former treatment of the plurality of former treatments to be chosen for each of the respective health conditions; (ii) an outcome score for each respective former treatment of the plurality of former treatments, wherein the outcome score for each respective former treatment is a measure of how the health data and/or the health condition of the respective former patient changed between the different points in time; (iii) a plurality of treatment recommendation scores comprising a respective treatment recommendation score for each respective former treatment based on the propensity score of each respective former treatment and the outcome score for each respective former treatment, wherein said training comprises generating a predictive model and a propensity score-based loss layer characterized by a loss associated with the predictive model, wherein the predictive model predicts an outcome of possible treatments, based on the propensity score, for treating the actual patient, wherein the neural network prevents, via a property of equivariance, a propensity score overfitting, wherein the equivariance uses a self-normalized Inverse Propensity Score (IPS) estimator (SNIPS) in which the determined propensity score is replaced by a true propensity score, wherein the true propensity score is determined via execution of an estimated translated Inverse Propensity Score (etIPS) algorithm in which an estimated propensity score-based risk in the loss layer is applied to learn the true propensity, and wherein the SNIPS estimator comprising the true propensity score is characterized by an invariance to translation of the loss.

2. The method according to claim 1, wherein a weighting is carried out in which the propensity score and the outcome score for each respective former treatment are weighted with a respective weighting score within a determination, during said training, of the treatment recommendation score for each respective former treatment.

3. The method according to claim 2, wherein the weighting is carried out with several different weighting scores, wherein a f inal weighting score is chosen from the several different weighting scores by a predetermined criterion, and wherein the final weighting score is used to weight the propensity score and the outcome score for each respective former treatment.

4. The method according to claim 3, wherein either the outcome score for one former treatment of the plurality of former treatments is a first outcome sore and the propensity score has a first weight or the outcome score for the one former treatment is a second outcome score and the propensity score has a second weight, and wherein the first outcome score exceeds the second outcome score and the first weight exceeds the second weight.

5. The method according to claim 1, wherein the health data, in the plurality of training data sets, includes static health data that is constant over time and sequential health data sequenced in a plurality time steps, said method further comprising: encoding, by the processor during said training, the sequential health data at each time step into a respective hidden state of the neural network, said hidden state having a dimension that is fine-tuned as a hyper-parameter in the neural network.

6. The method according to claim 1, said method further comprising: determining, by the processor during said training, a treatment matching factor, which is a measure for a discrepancy between the treatment recommendation score and the propensity score.

7. The method according to claim 6, said method further comprising outputting, by the processor during said training, an error message in response to the discrepancy represented by the treatment matching factor exceeding a predetermined limit.

8. The method according to claim 1, wherein each treatment recommendation score is determined during said training as a weighted combination of the propensity score and the outcome score, and wherein the propensity score is weighted relative to a weighting of the outcome score based on: the higher the outcome score is, the higher the propensity score 1 s weighted relative to the outcome score.

9. A computer-readable medium comprising instructions which, when executed by a processor, performs a computer-implemented method for providing a trained function to determine a candidate treatment recommendation for treating an actual patient, said computer-readable medium not being a transitory signal, said method comprising:

training, by the processor, a neural network using a plurality of training data sets respectively corresponding to a plurality of different former patients, each training data set being specific to a respective former patient of the plurality of different former patients, each training data set comprising treatment data pertaining to a former treatment of a plurality of former treatments chosen by a physician for the respective former patient, and each training data set comprising health data pertaining to a respective health condition of the respective former patient at different points in time, said using a plurality of training data sets including using the treatment data and the health data, said trained function comprising the neural network, said neural network determines treatment recommendation data that includes the candidate treatment recommendation for treating the actual patient, said training the neural network comprising determining parameters of the neural network, said parameters comprising: (i) a propensity score for each respective former treatment of the plurality of former treatments, wherein the propensity score represents a relative frequency for each respective former treatment of the plurality of former treatments to be chosen for each of the respective health conditions; (ii) an outcome score for each respective former treatment of the plurality of former treatments, wherein the outcome score for each respective former treatment is a measure of how the health data and/or the health condition of the respective former patient changed between the different points in time; (iii) a plurality of treatment recommendation scores comprising a respective treatment recommendation score for each respective former treatment based on the propensity score of each respective former treatment and the outcome score for each respective former treatment, wherein said training comprises generating a predictive model and a propensity score-based loss layer characterized by a loss associated with the predictive model, wherein the predictive model predicts an outcome of possible treatments, based on the propensity score, for treating the actual patient, wherein the neural network prevents, via a property of equivariance, a propensity score overfitting, wherein the equivariance uses a self-normalized Inverse Propensity Score (IPS) estimator (SNIPS) in which the determined propensity score is replaced by a true propensity score, wherein the true propensity score is determined via execution of an estimated translated Inverse Propensity Score (etIPS) algorithm in which an estimated propensity score-based risk in the loss layer is applied to learn the true propensity, and wherein the SNIPS estimator comprising the true propensity score is characterized by an invariance to translation of the loss.

10. A training system, comprising a processor, a memory, and a computer-readable medium comprising instructions which, when executed by the processor via the memory performs a computer-implemented method for providing a trained function to determine a candidate treatment recommendation for treating an actual patient, said method comprising:

training, by the processor, a neural network using a plurality of training data sets respectively corresponding to a plurality of different former patients, each training data set being specific to a respective former patient of the plurality of different former patients, each training data set comprising treatment data pertaining to a former treatment of a plurality of former treatments chosen by a physician for the respective former patient, and each training data set comprising health data pertaining to a respective health condition of the respective former patient at different points in time, said using a plurality of training data sets including using the treatment data and the health data, said trained function comprising the neural network, said neural network determines treatment recommendation data that includes the candidate treatment recommendation for treating the actual patient, said training the neural network comprising determining parameters of the neural network, said parameters comprising: (i) a propensity score for each respective former treatment of the plurality of former treatments, wherein the propensity score represents a relative frequency for each respective former treatment of the plurality of former treatments to be chosen for each of the respective health conditions; (ii) an outcome score for each respective former treatment of the plurality of former treatments, wherein the outcome score for each respective former treatment is a measure of how the health data and/or the health condition of the respective former patient changed between the different points in time; (iii) a plurality of treatment recommendation scores comprising a respective treatment recommendation score for each respective former treatment based on the propensity score of each respective former treatment and the outcome score for each respective former treatment, wherein said training comprises generating a predictive model and a propensity score-based loss layer characterized by a loss associated with the predictive model, wherein the predictive model predicts an outcome of possible treatments, based on the propensity score, for treating the actual patient, wherein the neural network prevents, via a property of equivariance, a propensity score overfitting, wherein the equivariance uses a self-normalized Inverse Propensity Score (IPS) estimator (SNIPS) in which the determined propensity score is replaced by a true propensity score, wherein the true propensity score is determined via execution of an estimated translated Inverse Propensity Score (etIPS) algorithm in which an estimated propensity score-based risk in the loss layer is applied to learn the true propensity, and wherein the SNIPS estimator comprising the true propensity score is characterized by an invariance to translation of the loss.

\* \* \* \* \*